United States Patent [19]

Kelly et al.

[11] Patent Number: 5,045,302

[45] Date of Patent: * Sep. 3, 1991

[54] LIGANDS AND CATIONIC COMPLEXES THEREOF WITH TECHNETIUM-99M

[75] Inventors: James D. Kelly, Amersham; Kwok W. Chiu, Gloucester; Ian A. Latham, West Bridgford, all of England

[73] Assignee: Amersham International plc, Buckinghamshire, England

[ * ] Notice: The portion of the term of this patent subsequent to Apr. 10, 2007 has been disclaimed.

[21] Appl. No.: 329,639

[22] Filed: Mar. 28, 1989

[30] Foreign Application Priority Data

Apr. 11, 1988 [GB] United Kingdom ............... 8808414

[51] Int. Cl.$^5$ ............... A61K 43/00; C07F 13/00
[52] U.S. Cl. ............................... 424/1.1; 534/14; 568/13; 568/70; 549/357; 549/415; 549/448; 549/472
[58] Field of Search ............... 568/8, 13; 556/70; 549/448, 415, 357, 472; 424/1.1; 534/15, 14

[56] References Cited

U.S. PATENT DOCUMENTS

| | | | |
|---|---|---|---|
| 4,451,450 | 5/1984 | Subramanyam | 568/13 |
| 4,526,776 | 7/1985 | Subramanyam et al. | 568/8 |
| 4,916,214 | 4/1990 | Chiu et al. | 424/1.1 |

FOREIGN PATENT DOCUMENTS 1917884  10/1969  Fed. Rep. of Germany.

*Primary Examiner*—Mukund J. Shah
*Assistant Examiner*—E. C. Ward
*Attorney, Agent, or Firm*—Wenderoth, Lind & Ponack

[57] ABSTRACT

This invention concerns novel bidentate ligands L having two phosphorus or arsenic atoms. Cationic complexes of the ligands with Technetium-99m, e.g. having the formula $[TcO_2L_2]^+$, are useful for body imaging, particularly myocardial imaging. The ligands have the general formula $$Y_2QZQY_2$$

where Q is phosphorus or
Z is a —CC— or —CCC— or —COC— groups,
the four groups Y are all C1–C8 saturated hydrocarbon or fluorohydrocarbon with 1–3 ether oxygen atoms.

10 Claims, No Drawings

LIGANDS AND CATIONIC COMPLEXES THEREOF WITH TECHNETIUM-99M

This invention relates to cationic complexes of technetium-99m (Tc-99m) useful as body imaging agents, and to bifunctional ligands useful in preparing such complexes.

Radiopharmaceuticals may be used as diagnostic or therapeutic agents by virtue of the physical properties of their constituent radionuclides. Thus, their utility is not based on any pharmacologic action. Most clinically used drugs of this class are diagnostic agents incorporating a gamma-emitting nuclide which because of physical or metabolic properties of its coordinated ligands, localises in a specific organ after intravenous injection. The resultant images can reflect organ structure or function. These images are obtained by means of a gamma camera that detects the distribution of ionising radiation emitted by the radioactive molecules. The principal isotope currently used in clinical diagnostic nuclear medicine is metastable technetium-99m ($t_{\frac{1}{2}}$ 6 hours).

It is well established that neutral bidentate ligands of the general type $R_2Q(CH_2)_nQR_2$ (where Q may be phosphorus or arsenic, and n is 2 or 3) form stable well characterised cationic complexes with $^{99}Tc$ and $^{99m}Tc$[1]. Several patents, including U.S. Pat. No. 4,481,184, U.S. Pat. No. 4,387,087, U.S. Pat. No. 4,489,054, U.S. Pat. No. 4,374,821, U.S. Pat. No. 4,451,450 and U.S. Pat. No. 4,526,776 describe various ligand species in which the coordinating atoms are phosphorus or arsenic, with predominantly alkyl and/or aryl substituents.

DE 1917884 mentions the compound $(CH_3OCH_2CH_2)_2P-CH_2CH_2-P(CH_2OCH_3)_2$ for use as a catalyst.

U.S. Pat. No. 4,916,214 concerns neutral bidentate donor ligands based on phosphorus or arsenic and which contain ether linkages; and cationic complexes of Tc-99 comprising these ligands. It was found that such complexes show suprising properties which may make them superior body imaging agents, particularly heart imaging agents, to comparable complexes not containing ether linkages. The present invention is concerned with a specific class of ligands, and their associated complexes with Tc-99m, within this general field.

In a first aspect, the invention provides a ligand having the formula $Y_2QZQY_2$, where each Q is phosphorus or arsenic, Z is a —CC— or —CCC— or —COC— chain or o-phenylene which may be substituted by C1–C4 alkoxy or alkoxyalkyl or spirocyclic ether, the groups Y may be the same or different and each is a saturated hydrocarbon or saturated fluorohydrocarbon which contains from 2 to 8 carbon atoms and from 1 to 3 ether oxygen atoms, provided that the four groups Y together contain a total of at least 13 carbon atoms. Preferably each group Y has the formula $$-[(CH_2)_m-(CR^1R^2)_l-O]_nR^3$$

where
l is 0 or 1,
m is 1 to 6,
provided that (l+m) is 1 to 6,
n is 1 to 3, where l is 0, $R^3$ is $-C_2H_5$ or $i-C_3H_7$ or $-CH_2-CH_xF_{3-x}$ where x is 0 to 2, or where l is 1, R1 and/or $R^2$ is $-CH_3$ or H and $R^3$ is $-CH_3$ or $-C_2H_5$ Preferably l is 0, m is 1 to 3, n is 1 and $R^3$ is $-C_2H_5$. A preferred example is the ligand called hereinafter P53, in which Q is phosphorus,
Z is $-C_2H_4-$, and
each Y is $-C_2H_4OC_2H_5$, thus having the formula

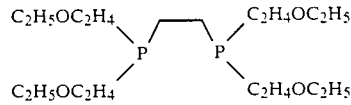

In other preferred groups of ligands:
Each group Y comprises a 5- or 6- membered ring of C and O atoms.

Each group Y has the formula:

$$-C_mH_{2m-1}((CH_2)_lOR^4)_2$$

where
m is 1 to 6
l is 0 or 1, such that (l+m) is 1 to 6,
$R^4$ is C1 to C3 alkyl or fluoroalkyl.

Q is phosphorus, and the two groups Y attached to each Q are different and are selected from those having the formula $$-(CH_2)_mOR^5$$

where m is 1 to 3, and $R^5$ is C1 to C4 alkyl or fluoroalkyl.

The ligands are preferably symmetrical about Z. In all cases, the four groups pendant to the phosphorus (or arsenic) atoms all contain ether oxygen atoms.

These ligands may be made by methods generally as described in the aforesaid U.S. Pat. No. 4,916,214. Ligands of the type $Y_2QZQY_2$ where all the groups Y are the same may be made by reacting one mole of the known compound bis(diphosphino)-ethane with four moles of an ether of appropriate formula containing an ethylenically unsaturated group. Symmetrical ligands where the groups Y are different may be made by reacting a known compound of the type Y(H)QZQ(H)Y with an alkyllithium and then reacting the product with a compound of the type YX where X is a monodentate ligand for Tc such as halogen.

The cationic complexes of Tc-99m may be prepared by methods known in the art. For example:

Complexes of the type $[TcO_2L_2]^+A^-$ may be prepared by methods as described in U.S. Pat. No. 4,374,821.

Complexes of the type $[TcL_3]^+A^-$ may be prepared by methods as described in U.S. Pat. No. 4,481,184.

Complexes of the type $[TcCl_2L_2]^+$ may be prepared by methods as described in U.S. Pat. Nos. 4,387,087 and 4,489,054.

In particular, the ligands are easily labelled to provide 1 - step room temperature syntheses of Tc-99m complexes. Once formed, the complexes are stable in aqueous media in forms which are suitable for administration. Complexes which have been prepared and shown to have particularly favourable properties for use as myocardial imaging agents include those believed to have the following formulae ($^{99m}$Tc is abbreviated to Tc):
a) [TcL$_2$O$_2$]$^+$, where L is the ligand P53; and
b) [TcCl$_2$L$_2$]$^+$ where L is the ligand P53.

The invention includes the complexes, which can be prepared as described in the Examples below, and which may or may not have these formulae.

Although this invention is concerned with results rather than with mechanisms, applicants offer the following as a possible explanation of mechanisms. Broadly, for compounds of similar structure, there is a relationship between lipophilicity and protein binding. Compounds of high lipophilicity are more strongly bound to proteins than compounds of low lipophilicity. For $^{99m}$Tc cations, the effect of high protein binding is that they remain a long time in circulation, so that the image of the heart muscle at convenient imaging times post-injection is obscured by the blood pool activity. A further generally observed tendency for the more highly lipophilic cations is that they possess slow clearance through the hepatobiliary system, so that heart imaging can be impaired by liver activity.

Substantially increasing the hydrophilicity of a $^{99m}$Tc complex has the desired effect reducing protein binding but also reduces heart uptake. It appears that there is, however, a region of intermediate lipophilicity where the heart uptake is retained and there is also absent, or sufficiently weak, protein binding to permit rapid clearance from blood. This can be illustrated by reference to the complexes noted above for TcL$_2$O$_2^+$(L=P53), a combination of the quite polar oxygens of the TcO$_2^+$ core (2 per molecule) with the eight ethoxy ether functions of the ligand, can achieve the desired combination of good heart uptake with low protein binding. By contrast, a complex of the type a) in which the ligand is an isomer of P53 in which each group Y is —C$_3$H$_6$OCH$_3$ (compound 2), has low heart uptake and substantially higher hydrophilicity, as indicated by a high urinary output.

It appears that there may be a ranking in contribution to polarity of TcO greater than MeO greater than EtO. By means of this background understanding, it is possible to achieve the required lipophilic/hydrophilic balance through the additive hydrophilic effects of the oxygen substituents balancing out the lipophilic effects of the hydrocarbon moieties in the molecule.

The following examples illustrate the invention.

EXAMPLE 1

Ligand Synthesis (EtOC$_2$H$_4$)$_2$P—C$_2$H$_4$—P(C$_2$H$_4$OEt)$_2$ (P53, Compound 1)

All reactions and manipulations were performed under vacuo or oxygen-free nitrogen atmosphere. Solvents were dried, and degassed by nitrogen purge prior to use. α-Azo-isobutyronitrile (AIBN) and ethyl vinyl ether were obtained from BDH and Aldrich respectively. Bis(diphosphino)-ethane was prepared according to the literature (1).

$^1$H nmr and $^{31}$P[$^1$H] nmr spectra were obtained from a Jeol 270 MHz machine Samples were dissolved in CDCl$_3$. $^1$H nmr was referenced internally to TMS and $^{31}$P[$^1$H] nmr was referenced externally to H$_3$PO$_4$.

Reaction Scheme

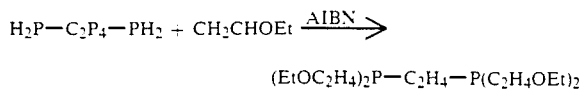

(EtOC$_2$H$_4$)$_2$P—C$_2$H$_4$—P(C$_2$H$_4$OEt)$_2$

A Fischer pressure-bottle equipped with a teflon stirring bar, was charged with ethyl vinyl ether (5 cm$^3$, 52.3 mmol), bis(diphosphino)ethane (1 cm$^3$, 10 mmol) and α-azo-isobutyronitrile (0.1 g, 0.61 mmol). The reaction mixture was then stirred and heated to 75° for 16 hours. After cooling back to room temperature, the viscous liquid was transferred to a 50 cm$^3$ round-bottomed flask. Removal of volatile materials was performed by heating under vacuum. The non-distillable material obtained is pure by nmr. Yield: 3.0 g, 80%. $^1$H nmr (CDCl$_3$):

| (ppm) | Integration | Assignment |
|---|---|---|
| 1.12 | 12H | Doublet of triplet, J = 1.16 Hz, 7.15 Hz, OCH$_2$C$\underline{H}_3$ |
| 1.51 | 4H | Broad multiplet, PC$_2$H$_4$P |
| 1.7 | 8H | Broad triplet, J = 7.4 Hz PC$\underline{H}_2$CH$_2$OEt |
| 3.4 | 8H | Doublet of quartet, J = 1.16 Hz, 7.15 Hz, OC$\underline{H}_2$CH$_3$ |
| 3.49 | 8H | Broad multiplet, PCH$_2$C$\underline{H}_2$OEt |

$^{31}$P[$^1$H] nmr δ = −33.17 ppm

Compounds 2 to 38 were prepared similarly and were characterised by $^1$H and $^{31}$P NMR (see Table 1). The required unsaturated ether precursors are either commercially available or literature compounds. The preparation of vinyl ethers has been reviewed (reference 2). The most widely applicable methods of synthesis are KOH elimination from the corresponding β-haloether (reference 3) and vinyl exchange (reference 4). Allylic ethers are readily prepared using phase transfer methods (references 5, 6).

Reference 1 = Inorganic Synthesis, Vol 14, 10.

2. P. Fischer in "The Chemistry of Ethers, Crown Ethers, Hydroxy Compounds and their Sulphur Analogues". Part 2 (1980). S. Patai (Ed.), p. 761.

3. R. E. Ireland and D. Habich, Chem. Ber., 114, 1418 (1981).

4. W. H. Watanabe and L. E. Conlon, J. Am. Chem. Soc., 79, 2828 (1957).

5. A. Merz, Ang. Chem. Int. Ed. Engl., 12, 846 (1973).

6. B. Boutevin et al., J. Fluorine Chem., 35, 399 (1987).

EXAMPLE 2

[TcO$_2$L$_2$]$^+$
Technetium V diphosphine dioxo complex

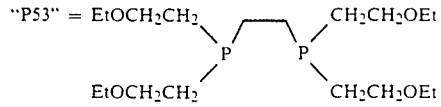

Materials
Saline = 3.5 ml
"P53" = 10 μl $^{99m}$Tc O$_4^{(-)}$Na$^+$ generator elute 1.5 ml at 1.19 GBq/ml Method These constituents were placed in a septum-sealed glass vial under nitrogen and stood at room temperature for 30 minutes (pH=6.8). The resulting solution was submitted to various analytical techniques, summarised as below:

Chromatography Data

The resulting solutions (above) contain no colloid or free $^{99m}$TcO$_4^{(-)}$, and indicates that the technetium complex is present in solution in approximately 92% yield.

| Saline | rf = 0.00 |
| Methylethylketone | rf = 0.70 |
| Acetonitrile/water 50:50 | rf = 1.00 |

HPLC Data

The complex elutes as a sharp peak at approximately 7.2 minutes

Gel Electrophoresis Data

The complex moved as a single band towards the cathode rf=−0.44 (−indicating movement towards cathode).

Biodistribution Results

See Tables 2 and 3.

EXAMPLE 3

Plasma binding studies 1 ml sample of guinea pig or human plasma or saline (control) were added to 2 ml Eppendorf tubes. To these were then added 100 ul aliquots of the $^{99m}$Tc preparation being studied. Mixing was performed by inverting the tubes several times. A 50 ul sample was then taken for counting and the remainder of the sample (1050 ul) was quantitatively transferred to the top of the PD10 column. The sample was allowed to enter the column matrix and then washed in with 1.5 mls saline. Initially a 2.5 ml aliquot was collected for counting, (dead volume) subsequently 0.5 ml aliquots were collected until a total volume of 16 mls had been used to elute the column. Routinely, for a complex which does not bind non-specifically, i.e. irreversibly, to the components of the column, this treatment is sufficient to quantitatively elute all activity loaded onto the column. Collected fractions were counted in a $\gamma$ well counter and a graph plotted of percentage recovery was calculated from initial preloading sample and cumulative counts.

The percent recovery of Tc99m activity obtained when using complex a) based on the P53 ligand was as follows:

saline (control)—90.82%
human plasma—65.23%
guinea pig serum—90.34%.

Though lower than the other two, the recovery figure from human serum is regarded as satisfactory and as indicating no significant binding of the complex a) to any component of human plasma.

EXAMPLE 4

Tc-99m complexes of formula [TcO$_2$L$_2$]$^+$ were made by the general method of Example 2, but using the compounds 2 to 38 in place of compound 1 (P53). Rat biodistribution properties of the resulting complexes are reported in Table 4.

EXAMPLE 5

Technetium III diphosphine dichloro-complex [TcCl$_2$L$_2$]$^+$

Technetium III diphosphine dichloro-complex [TcCl$_2$L$_2$]$^-$

L = P53:

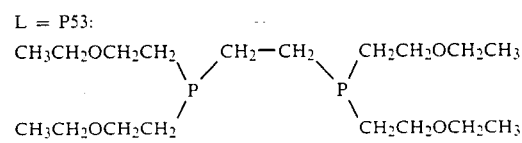

SYNTHESIS

Materials

| FeCl$_3$.6H$_2$O | 5 mg |
| P53 | 10 μl |
| EGTA | 15 mg |
| NaCl | 100 mg |
| EtOH | 2 ml |
| $^{99m}$TcO$_4^-$ (aq) | 0.4 ml ~ 4 BGq Generator Eluate |
| Saline | 2.6 ml |

EGTA = Ethylene glycol-O,O'-bis(2-aminoethyl)-N,N,N',N' -tetraacetic acid

A purple ethanolic solution of FeCl$_3$ and P53 was prepared, and added to an aqueous solution containing the remaining reactants. The resulting mixture was heated at 120° C. for 60 minutes, changing colour to pale yellow. The products were submitted to various analytical techniques, summarised below:

Chromatography

The resulting solutions (above) contain no colloid or free $^{99m}$TcO$_4^-$, indicating that the technetium complex is present in solution in approximately 85-95% yield.

| Saline | rf = 0.10 |
| Methylethyl ketone | rf = 0.75 |
| Acetonitrile/Water (50:50) | rf = 0.9 (broad) |

HPLC Data:

The complex elutes as a sharp peak at 9.8 minutes (<10% impurity peak at 8.9 minutes).

Gel Electrophoresis Data:

The complex moves as a single species towards the cathode rf=−0.42 (−indicating movement towards cathode).

Biodistribution Results:

Table 5 In Rats—The Tc$^{III}$—P53 complex shows good heart uptake in rats and guinea pigs, good Table 6 In Guinea Pigs—blood and liver clearance, but washes out of the respective hearts.

Plasma Binding Results:

This complex shows a possible slight interaction with human plasma (Recovery 93.8%).

TABLE 1

$Y_2QZQY_2$

| No/Cmpd | Y | $^{31}P$ NMR δ/ppm | $^1H$ NMR: δ (ppm) | | | | | | |
|---|---|---|---|---|---|---|---|---|---|
| | | | CHP.CH₂P | OCH₂ | OCH | OMe | OCH₂CH₃ | CH₂CH₂ | Other |
| | | | For Q = P, Z = CH₂CH₂ | | | | | | |
| 1 | —CH₂CH₂OEt | −33.1 | 1.7(m) 1.5(m) | 3.5(m) 3.4(q) | | | 1.1(t) | | |
| 2 | —CH₂CH₂OMe | −33.0 | 1.77(m) 1.58(m) | 3.56(m) | | 3.34(s) | | | |
| 3 | —CH₂CH₂CH₂OMe | −28.5 | 1.75(m) 1.55(m) | 3.3(t) | | 3.2(s) | | 1.48(m) | |
| 4 | —CH₂CH₂CH₂OEt | −26.0 | 1.8(m) 1.6(m) | 3.4(m) | | | 1.2(t) | 1.4(m) | |
| 5 | —CH₂OEt | −30.6 | 1.78(m) | 3.6(q) 3.9(m) | | | 1.3(t) | | |
| 6 | —CH=CHOEt | −55.1 | 6.47 2.75(m) | 3.9(q) | 4.61 | | 1.3(t) | | |
| 7 | —CH₂CH₂OCH₂CH₂OMe | −33.0 | 1.73(t) 1.5(m) | 3.5(m) | | 3.3(s) | | | |
| 8 | —CH₂CH₂OCH₂CH₂OEt | −34.0 | 1.7(t) 1.5(m) | 3.5(m) | | | 1.15(t) | | |
| 9 | —CH₂CH₂OCF₂CF₂H | −32.1 | 1.85(t) 1.55(t) | 4.1(m) | | | | | CF₂H 5.62(tt) |
| 10 | —CH₂CH₂CH₂OCH₂CF₃ | −26.9 | 1.6(m) 1.5(m) | 3.75(q) 3.6(t) | | | | | |
| 11 | —CH₂CHMeOMe | −34.6 | 1.7(m) 1.5(m) | | 3.4(m) | 3.3(s) | | | Me 1.08(d) |
| 12 | —CH₂CHEtOMe | −25.3 | 1.57(m) | 3.2(m) | | 3.4(s) | 0.98(t) | | |
| 13 | —CH₂CHMeOEt | −33.6 −34.4 | 1.70(m) 1.48(m) | 3.30(m) | 4.50(m) | | 1.12(t) | | Me 1.18(d) |
| 14 | —CH₂CHMeCH₂OMe | −37.1 | 1.7(m) 1.5(m) | 3.2(m) | | 3.3(s) | | | Me 0.98(d) |
| 15 | —CH₂CH₂CHMeOMe | −25.3 | 1.42(m) | | 3.3(m) | 3.2(s) | | | Me 1.08(d) |
| 16 | —CH₂CH₂CMe₂OMe | −22.7 | 1.5(m) 1.3(m) | | | 3.1(s) | | 1.15(m) | CMe₂ 1.09(s) |
| 17 | —CH₂CH(CH₂OMe)₂ | −35.8 | 1.8(m) 1.37(m) | 3.65(m) 3.3(m) | | 3.2(s) | | | CH₂CH 1.1(m) |
| 18 | —CH₂CH(CH₂OEt)₂ | −35.7 | 1.9(m) 1.4(m) | 3.4(m) | | | 1.1(t) | | CH₂CH 1.15(m) |
| 19 | —CH₂CH₂CH(OMe)₂ | −25.3 | 1.8(m) 1.6(m) | | 4.43(t) | 3.38(s) | | | |
| 20 | —CH₂CH₂CH(OEt)₂ | −25.3 | 1.7(m) 1.4(m) | 3.5(m) | 4.45(t) | | 1.15(t) | | |
| 21 | —CH₂-(1,3-dioxolane) | −34.3 −35.2 | 1.75(d) 1.60(m) | 3.9(brs) 3.4(brs) | 4.1(brs) | | | | OCH₂O 4.70,4.85(s) |
| 22 | —CH₂-(2,2-dimethyl-1,3-dioxolane) | −36.0 (m) | 1.75(d) | 3.55(m) | 4.1(m) | | | | CMe₂ 1.40,1.25(s) |
| 23 | —CH₂-(tetrahydrofuran-3-yl) | −8.9 (m) | 2.13(m) | 3.75(m) | | | | 1.6(m) | |
| 24 | —CH₂-(tetrahydrofuran-2-yl) | −34.5 (m) | 1.5(m) 1.9(m) | 3.80(m) | 3.55(m) | | | 1.7(m) | |
| 25 | —CH₂-(tetrahydropyran-4-yl) | −39.5 (m) | 1.85 1.7 | 3.5(t) | | | | 1.45(m) | CH₂CH 1.56(m) |
| 26 | —CH₂-(1,3-dioxan-2-yl) | −33.4 | 1.5(m) | 3.6(m) | 3.2(m) | | | | |
| 27 | —CH₂CH₂OMe | −32.4 | 2.0(m) | 3.6(m) | | 3.17(s) | | | |

TABLE 1-continued $Y_2QZQY_2$

| No/Cmpd | Y | $^{31}P$ NMR δ/ppm | $^1H$ NMR: δ (ppm) | | | | | | |
|---|---|---|---|---|---|---|---|---|---|
| | | | CHP.CH$_2$P | OCH$_2$ | OCH | OMe | OCH$_2$CH$_3$ | CH$_2$CH$_2$ | Other |
| | —CH$_2$OMe | | 1.8(m) | | | 3.19(s) | | | |
| 28 | —CH$_2$CH$_2$OMe | −33.4 | 1.85(t) | 3.4(q) | | 3.2(s) | 1.2(t) | | |
| | —CH$_2$CH$_2$OEt | | 1.7(t) | 3.6(m) | | | | | |
| 29 | —CH$_2$CH$_2$OMe | −32.9 | 1.7(m) | 3.5(m) | | 3.27(s) | 0.89(t) | | |
| | —CH$_2$CH$_2$OPr | | 1.5(m) | 3.3(m) | | | | | |
| 30 | —CH$_2$CH$_2$OMe | −30.7 | 1.7(m) | 3.5(m) | | 3.37(s) | 1.1(t) | | |
| | —CH$_2$CH$_2$CH$_2$OEt | | 1.5(m) | | | | | | |
| 31 | —CH$_2$CH$_2$OEt | −32.9 | 1.7(m) | 3.48(m) | | | 1.1(t) | | CMe$_2$ 1.18(m) |
| | —CH$_2$CH$_2$OiPr | | 1.5(m) | 3.37(q) | | | | | |
| 32 | —CH$_2$CH$_2$OEt | −32.8 | 1.7(m) | 3.5(m) | | | 1.12(t) | | CH$_2$F 4.5(dt) |
| | —CH$_2$CH$_2$OCH$_2$CH$_2$F | | 1.5(t) | 3.41(q) | | | | | |
| For Q = P, Z = CH$_2$CH$_2$CH$_2$ | | | | | | | | | |
| 33 | —CH$_2$OEt | −35.2 | 1.78(m) | 3.84(m) | | | 1.33(m) | | |
| | | | | 3.64(q) | | | | | |
| 34 | —CH$_2$CH$_2$OEt | −39.0 | 1.8(m) | 3.6(m) | | | 1.15(t) | | |
| | | | 1.55(m) | 3.4(q) | | | | | |
| 35 | —CH$_2$-(tetrahydrofuran) | −32.0 (m) | 1.8(m) | 3.65(m) | 3.85(m) | | | 1.5(m) 1.2(m) | |
| For Q = P, Z = CH$_2$CH(OMe)CH$_2$ | | | | | | | | | |
| 36 | —CH$_2$CH$_2$OEt | −40.9 | 1.8(m) | 3.5(m) | | 3.37(m) | 1.1(t) | | |
| For Q = P, Z = o phenylene | | | | | | | | | |
| 37 | —CH$_2$CH$_2$OEt | −45.1 | 2.3(m) | 3.65(m) | | | 1.1(t) | | Arom 7.2(m) |
| | | | | 3.25(q) | | | | | |
| 38 | —CH$_2$CH$_2$CH$_2$OEt | −38.0 | 1.9(m) | 3.5(m) | | | 1.15(t) | 1.8(m) | Arom 7.3(m) |
| | | | | 3.4(q) | | | | | |

TABLE 2

Animal Biodistribution Data in Rat $[TcO_2(P53)_2]^-$

'P53'  $C_2H_5OC_2H_4$ , $C_2H_5OC_2H_4$ — P—P — $C_2H_4OC_2H_5$ , $C_2H_4OC_2H_5$

| Time p.i. in vivo | 2 min | | 60 min | |
|---|---|---|---|---|
| | Mean | Std. dev. | Mean | Std. dev. |
| % Injected dose/organ | | | | |
| Heart | 1.66 | 0.11 | 1.68 | 0.13 |
| Blood | 2.25 | 0.43 | 0.28 | 0.00 |
| Muscle | 31.6 | 9.3 | 31.6 | 2.4 |
| Lung | 1.44 | 0.05 | 0.65 | 0.20 |
| Liver | 14.1 | 1.3 | 1.62 | 0.34 |
| Liver + GI | 37.8 | 2.9 | 42.5 | 3.5 |
| Kidney + Urine | 13.2 | 1.8 | 9.29 | 2.53 |
| Brian | 0.03 | 0.05 | 0.02 | 0.01 |
| Counts/Gram Ratio | | | | |
| Heart/Blood | 10.5 | 1.8 | 86.4 | 9.8 |
| Heart/Muscle | 5.94 | 2.57 | 5.74 | 0.93 |
| Heart/Liver | 1.52 | 0.08 | 14.4 | 1.8 |
| Heart/Lung | 2.0 | 0.3 | 4.3 | 1.9 |

TABLE 3

Animal Biodistribution Data in Guinea Pig $[TcO_2(P53)_2]^-$

'P53'  $C_2H_5OC_2H_4$ , $C_2H_5OC_2H_4$ — P—P — $C_2H_4OC_2H_5$ , $C_2H_4OC_2H_5$

| Time p.i. in vivo | 2 min | | 60 min | |
|---|---|---|---|---|
| | Mean | std. dev. | Mean | std. dev. |
| % Injected dose/organ | | | | |
| Heart | 1.33 | 0.14 | 0.99 | 0.12 |
| Blood | 3.11 | 0.80 | 0.41 | 0.07 |
| Muscle | 30.0 | 4.4 | 43.4 | 28.4 |
| Lung | 1.14 | 0.19 | 0.47 | 0.03 |
| Liver | 11.6 | 2.5 | 2.13 | 0.56 |
| Liver + GI | 38.7 | 4.1 | 44.6 | 2.8 |
| Kidney + Urine | 16.7 | 1.2 | 16.1 | 1.4 |
| Brain | — | — | — | — |
| Counts/Gram Ratio | | | | |
| Heart/Blood | 10.9 | 2.7 | 61.9 | 12.0 |
| Heart/Muscle | 6.12 | 0.44 | 4.10 | 2.09 |
| Heart/Liver | 1.90 | 0.87 | 7.51 | 2.40 |
| Heart/Lung | 1.2 | 0.2 | 2.0 | 0.2 |

TABLE 4

RAT BIODISTRIBUTION OF $TcO_2(PHOSPHINE)_2^-$

| | % Injected dose/organ | | | | | | Counts/g ratio | | | |
|---|---|---|---|---|---|---|---|---|---|---|
| | HEART | | BLOOD | | LIVER | | HEART/BLOOD | | HEART/LIVER | |
| Cmpd | 2 min | 60 min | 2 min | 60 min | 2 min | 60 min | 2 min | 60 min | 2 min | 60 min |
| 1 | 1.66 | 1.68 | 2.25 | 0.28 | 14.1 | 1.62 | 10.5 | 86.4 | 1.52 | 14.4 |
| 2 | 0.66 | 0.17 | 19.85 | 0.54 | 5.90 | 2.37 | 0.44 | 5.4 | 1.57 | 1.17 |
| 3 | 0.44 | 0.09 | 18.8 | 0.77 | 3.62 | 1.35 | 0.35 | 1.82 | 1.71 | 0.88 |
| 4 | 1.00 | 0.96 | 7.46 | 0.73 | 18.8 | 6.96 | 1.96 | 20.0 | 0.81 | 2.13 |
| 5 | 0.54 | 0.27 | 12.4 | 1.63 | 33.1 | 8.85 | 0.68 | 2.6 | 0.20 | 0.37 |
| 6 | 0.58 | 0.46 | 15.6 | 3.26 | 44.3 | 30.6 | 0.61 | 2.2 | 0.18 | 0.19 |
| 8 | 0.54 | 0.42 | 11.0 | 1.69 | 19.0 | 12.0 | 0.72 | 4.0 | 0.41 | 0.46 |
| 10 | 0.43 | 0.14 | 40.5 | 7.59 | 35.2 | 48.8 | 0.17 | 0.3 | 0.16 | 0.04 |
| 11 | 0.31 | 0.62 | 9.45 | 1.93 | 20.3 | 12.0 | 1.27 | 5.70 | 0.57 | 0.75 |
| 12 | 0.70 | 0.48 | 11.7 | 1.63 | 25.2 | 9.72 | 1.04 | 4.7 | 0.39 | 0.63 |

TABLE 4-continued

RAT BIODISTRIBUTION OF TcO$_2$(PHOSPHINE)$_2$$^-$

| | % Injected dose/organ | | | | | | Counts/g ratio | | | |
|---|---|---|---|---|---|---|---|---|---|---|
| | HEART | | BLOOD | | LIVER | | HEART/BLOOD | | HEART/LIVER | |
| Cmpd | 2 min | 60 min | 2 min | 60 min | 2 min | 60 min | 2 min | 60 min | 2 min | 60 min |
| 13 | 1.21 | 0.96 | 7.17 | 1.77 | 22.0 | 10.6 | 2.54 | 7.9 | 0.70 | 1.25 |
| 14 | 0.41 | 0.05 | 15.4 | 1.02 | 5.80 | 1.54 | 0.41 | 0.7 | 0.98 | 0.39 |
| 15 | 0.62 | 0.51 | 12.2 | 0.67 | 8.22 | 2.24 | 0.70 | 9.4 | 1.01 | 2.48 |
| 16 | 0.79 | 0.54 | 11.4 | 1.58 | 19.2 | 7.71 | 1.01 | 4.69 | 0.58 | 0.96 |
| 17 | 1.14 | 0.86 | 5.86 | 1.03 | 17.1 | 7.88 | 2.99 | 13.9 | 0.92 | 1.59 |
| 18 | 0.58 | 0.41 | 24.2 | 5.78 | 35.1 | 36.0 | 0.37 | 1.0 | 0.24 | 0.14 |
| 19 | 0.46 | 0.03 | 18.8 | 0.88 | 3.27 | 0.67 | 0.37 | 0.6 | 1.29 | 0.76 |
| 20 | 1.01 | 0.81 | 7.14 | 1.52 | 24.50 | 14.90 | 1.95 | 7.9 | 0.50 | 0.69 |
| 21 | 0.37 | 0.04 | 18.6 | 1.14 | 9.83 | 1.95 | 0.33 | 0.5 | 0.58 | 0.26 |
| 22 | 0.99 | 1.00 | 10.4 | 1.23 | 15.7 | 3.41 | 1.20 | 12.3 | 0.79 | 3.99 |
| 24 | 1.82 | 1.42 | 3.92 | 0.55 | 16.4 | 8.56 | 6.98 | 39.7 | 1.74 | 2.62 |
| 25 | 0.40 | 0.04 | 18.10 | 1.51 | 5.74 | 1.60 | 0.34 | 0.41 | 0.94 | 0.34 |
| 28 | 0.82 | 0.69 | 9.0 | 0.73 | 11.0 | 2.94 | 1.62 | 15.5 | 1.28 | 3.93 |
| 29 | 1.23 | 1.15 | 8.75 | 1.64 | 18.6 | 11.5 | 2.26 | 11.5 | 0.95 | 1.40 |
| 30 | 0.73 | 0.70 | 9.52 | 0.34 | 7.69 | 1.89 | 1.14 | 27.4 | 1.28 | 4.24 |
| 31 | 1.21 | 0.99 | 6.88 | 1.22 | 25.0 | 12.4 | 3.05 | 13.4 | 0.84 | 1.21 |
| 32 | 0.85 | 0.81 | 5.85 | 0.38 | 10.8 | 1.78 | 2.31 | 33.2 | 1.27 | 7.46 |
| 33 | 0.50 | 0.29 | 17.9 | 3.20 | 39.4 | 11.4 | 0.43 | 1.3 | 0.16 | 0.29 |
| 34 | 0.41 | 0.16 | 19.5 | 4.56 | 29.7 | 10.9 | 0.34 | 0.52 | 0.22 | 0.21 |
| 35 | 0.59 | 0.32 | 10.5 | 1.44 | 28.2 | 10.7 | 0.88 | 3.8 | 0.28 | 0.46 |
| 36 | 1.05 | 0.73 | 10.8 | 2.18 | 18.8 | 6.64 | 1.45 | 5.69 | 0.73 | 1.62 |
| 37 | 0.82 | 0.54 | 12.4 | 3.25 | 29.7 | 12.0 | 0.99 | 2.62 | 0.35 | 0.63 |

TABLE 5

ANIMAL BIODISTRIBUTION DATA IN RAT
Complex: [Technetium III dichloro-(P53)$_2$]$^-$ cation

| Time p.i. | 2 min | | 60 min | |
|---|---|---|---|---|
| in vivo | Mean | Std. Dev. | Mean | Std. Dev. |
| | % injected dose/organ | | | |
| Heart | 1.51 | 0.20 | 0.16 | 0.01 |
| Blood | 5.24 | 0.11 | 0.71 | 0.03 |
| Muscle | 34.92 | 12.89 | 11.68 | 1.69 |
| Lung | 1.45 | 0.08 | 0.47 | 0.18 |
| Liver | 28.87 | 4.71 | 4.78 | 0.28 |
| Liver + GI | 41.13 | 5.54 | 61.34 | 0.90 |
| Kidney + Urine | 4.48 | 0.56 | 4.95 | 1.00 |
| | Counts/Gram ratio | | | |
| Heart/Blood | 3.90 | 0.45 | 3.09 | 0.07 |
| Heart/Muscle | 4.68 | 1.40 | 1.41 | 0.20 |
| Heart/Liver | 0.64 | 0.10 | 0.46 | 0.03 |

TABLE 6

ANIMAL BIODISTRIBUTION IN GUINEA PIG
Complex: [Technetium III-dichloro(P53)$_2$]$^-$ cation

| Time p.i. | 2 min | | 60 min | |
|---|---|---|---|---|
| in vivo | Mean | Std. Dev. | Mean | Std. Dev. |
| | % injected dose/organ | | | |
| Heart | 1.89 | 0.27 | 0.13 | 0.01 |
| Blood | 3.50 | 0.64 | 0.58 | 0.09 |
| Muscle | 61.65 | 19.29 | 15.16 | 2.19 |
| Lung | 3.11 | 0.46 | 0.30 | 0.04 |
| Liver | 13.74 | 2.81 | 3.16 | 0.71 |
| Liver + GI | 18.72 | 4.54 | 62.38 | 19.4 |
| Kidney + Urine | 6.98 | 1.49 | 3.20 | 1.07 |
| | Counts/Gram ratio | | | |
| Heart/Blood | 12.72 | 1.68 | 5.35 | 1.08 |
| Heart/Muscle | 4.48 | 2.44 | 1.13 | 0.17 |
| Heart/Liver | 2.13 | 0.44 | 0.72 | 0.19 |

We claim:
1. A ligand having the formula

$$Y_2QZQY_2$$

where each Q is phosphorus,

Z is a —CC— or —CCC— chain or o-phenylene which may be substituted by C1-C3 alkoxy or alkoxyalkyl, the groups Y may be the same or different and each is a saturated hydrocarbon or saturated fluorohydrocarbon which contains from 2 to 8 carbon atoms and from 1 to 3 ether oxygen atoms, provided that the four groups Y together contain a total of at least 13 carbon atoms.

2. A ligand as claimed in claim 1, wherein the groups Y may be the same or different and each has the formula $$-[(CH_2)_m-(CR^1R^2)_l-O]_nR^3$$

where
l is 0 or 1,
m is 1 to 3,
provided that (l+m) is 1 to 3,
n is 1 or 2,
where l is 0, $R^3$ is —C$_2$H$_5$ or i—C$_3$H$_7$ or —CH$_2$—CH$_x$F$_{3-x}$
where x is 0 to 2, or
where l is 1, $R^1$ and/or $R^2$ is —CH$_3$ or H and $R^3$ is —CH$_3$ or —C$_2$H$_5$ 3. A ligand as claimed in claim 2, where m is 1 to 3 and n is 1.

4. A ligand as claimed in claim 2, wherein
Q is phosphorus,
Z is —C$_2$H$_4$—,
each Y is —C$_2$H$_4$OC$_2$H$_5$.

5. A ligand as claimed in claim 1, wherein each group Y comprises a 5- or 6- membered alicyclic ring containing 1 or 2 ether oxygen atoms.

6. A ligand as claimed in claim 1, wherein each group Y has the formula:

$$-C_mH_{2m-1}((CH_2)_lOR^4)_2$$

where
m is 1 to 3
l is 0 to 1, such that (l+m) is 1 to 3.
$R^4$ is C1 to C3 alkyl or fluoroalkyl.

7. A ligand as claimed in claim 1, wherein Q is a phosphorus, and the two groups Y attached to each Q are different and are selected from those having the formula —(CH$_2$)$_m$ O R$^5$ where m is 1 to 3, and R$^5$ is C1 to C4 alkyl or fluoroalkyl.

8. A cationic complex of technetium-99m with a ligand according to claim 1.

9. A complex as claimed in claim 8 having the formula [TcL$_2$X$_2$]$^+$ or [TcL$_2$O$_2$]$^+$ where L is the ligand and X is a monodentate ligand for Tc.

10. A complex as claimed in claim 8, having the formula [TcL$_2$O$_2$]$^+$ where L is a ligand having the formula (C$_2$H$_5$OC$_2$H$_4$)$_2$ P—C$_2$H$_4$—P(C$_2$H$_4$OC$_2$H$_5$)$_2$.

* * * * *